(12) United States Patent
Parenteau et al.

(10) Patent No.: US 7,597,712 B2
(45) Date of Patent: Oct. 6, 2009

(54) METHOD FOR TREATING A PATIENT USING A CULTURED CONNECTIVE TISSUE CONSTRUCT

(75) Inventors: Nancy L. Parenteau, Wayland, MA (US); James T. Robertson, Memphis, TN (US)

(73) Assignee: Organogenesis, Inc., Canton, MA (US)

( * ) Notice: Subject to any disclaimer, the term of this patent is extended or adjusted under 35 U.S.C. 154(b) by 0 days.

(21) Appl. No.: 09/955,414

(22) Filed: Sep. 18, 2001

(65) Prior Publication Data
US 2002/0082698 A1 Jun. 27, 2002

Related U.S. Application Data

(60) Provisional application No. 60/233,401, filed on Sep. 18, 2000.

(51) Int. Cl.
*A61F 2/44* (2006.01)
(52) U.S. Cl. .................. 623/17.11; 623/17.16; 435/1.1; 435/395
(58) Field of Classification Search ............... 623/17.11, 623/17.16; 435/1.1, 395
See application file for complete search history.

(56) References Cited

U.S. PATENT DOCUMENTS

| | | | | |
|---|---|---|---|---|
| 4,485,096 A | * | 11/1984 | Bell | 424/532 |
| 4,963,489 A | | 10/1990 | Naughton et al. | 435/240 |
| 5,863,984 A | * | 1/1999 | Doillon et al. | 525/54.1 |
| 6,110,210 A | * | 8/2000 | Norton et al. | 623/17.16 |
| 6,197,586 B1 | * | 3/2001 | Bhatnagar et al. | 435/395 |
| 6,352,557 B1 | * | 3/2002 | Ferree | 623/17.11 |
| 6,533,817 B1 | * | 3/2003 | Norton et al. | 623/17.16 |
| 6,592,625 B2 | * | 7/2003 | Cauthen | 623/17.16 |
| 7,220,281 B2 | * | 5/2007 | Lambrecht et al. | 623/17.16 |
| 2002/0172705 A1 | * | 11/2002 | Murphy et al. | 424/422 |
| 2005/0038519 A1 | * | 2/2005 | Lambrecht et al. | 623/17.16 |
| 2007/0100348 A1 | * | 5/2007 | Cauthen et al. | 606/99 |

FOREIGN PATENT DOCUMENTS

| | | |
|---|---|---|
| EP | 0 418 035 A1 | 3/1991 |
| WO | WO 91/16867 | 11/1991 |
| WO | WO 98/40111 | 9/1998 |
| WO | WO 99/04720 * | 2/1999 |
| WO | WO 00/29553 | 5/2000 |
| WO | WO 00/51527 | 9/2000 |

OTHER PUBLICATIONS

Abstract of Johnson et al "Secretory cells in the nucleus pulposis of adult human intervertebral disc. A preliminary report" Acta Anat (Basel) 125(3):161-164, (1986).*
Parenteau et al., "The Organotypic Culture of Human Skin Keratinocytes and Fibroblasts to Achieve Form and Function," Crytotechnology, Kluwer Academic Publishers, 1992, vol. 9, pp. 163-171.

* cited by examiner

*Primary Examiner*—Paul Prebilic
(74) *Attorney, Agent, or Firm*—Edward J. Adamson; Ravi A. Dipali

(57) ABSTRACT

The invention is directed to a method of tissue replacement and repair using a cultured bioremodelable connective tissue construct. The invention is specifically directed to a method for repairing annulus fibrosis of the intervertebral disc, after discectomy surgery where the annulus fibrosis has been opened, with a cultured bioremodelable connective tissue construct.

13 Claims, 1 Drawing Sheet

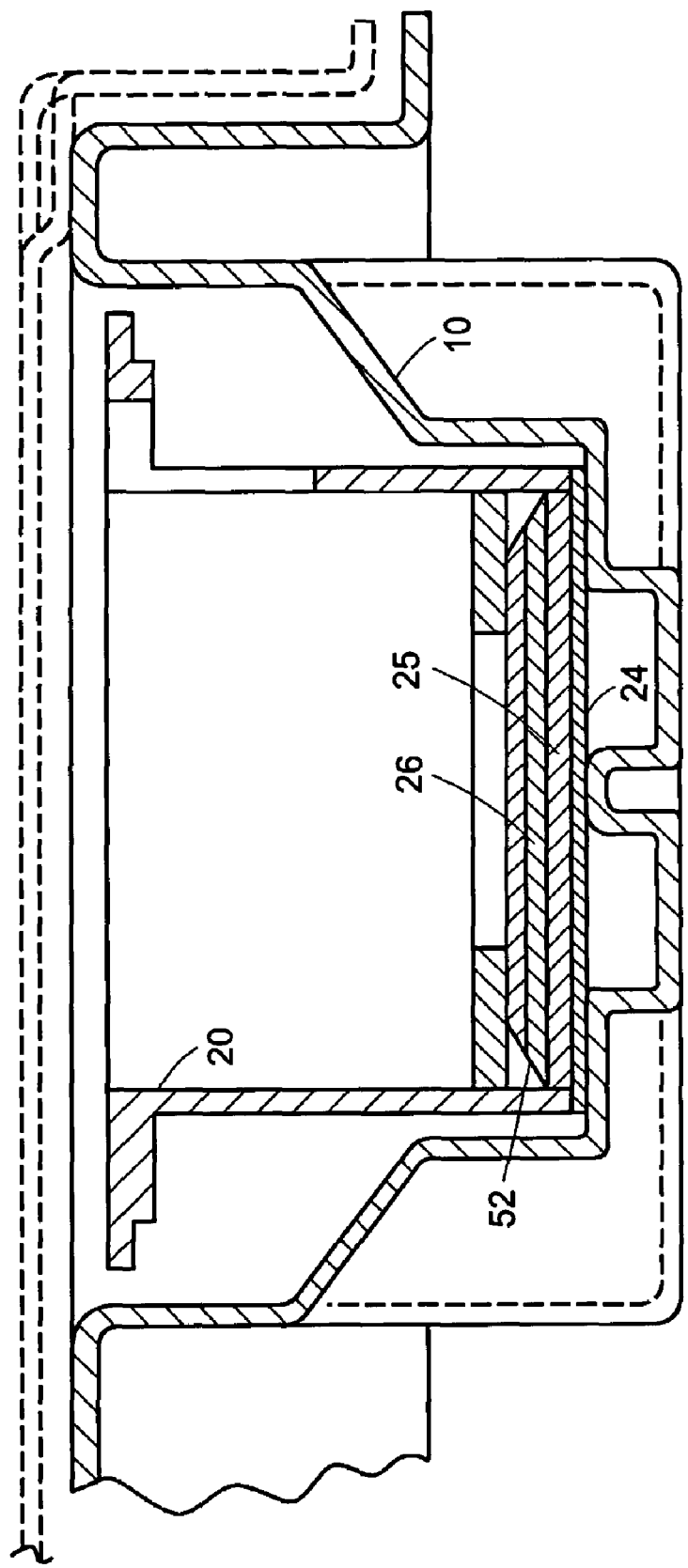

METHOD FOR TREATING A PATIENT USING A CULTURED CONNECTIVE TISSUE CONSTRUCT

CROSS-REFERENCE TO RELATED APPLICATIONS

This application claims the benefit of U.S.S.N. 60/233,401, filed Sep. 18, 2000.

FIELD OF THE INVENTION

The invention is in the field of tissue engineering, particularly the use of a cultured living connective tissue construct in surgical repair indications.

BACKGROUND OF THE INVENTION

Intervertebral disc injuries are painful, debilitating and costly to the patient. The intervertebral disc lies between the articular surfaces of adjacent vertebral bodies. The disc consists of concentric layers of collagen fibers, the annulus fibrosis, and the central nucleus pulposus, which it surrounds. The nucleus pulposus consists of a viscous fluid connective tissue matrix and cells. The cells of the nucleus pulposus, physaliphorous cells, are scattered in irregular aggregates throughout the extracellular matrix consisting of ground substance. On the exterior of the vertebrae, the annulus fibrosis and the vertebrae are supported peripherally by longitudinal ligaments that run the parallel to the spine.

The intervertebral disc functions in the manner of a hydraulic shock absorber with the nucleus pulposus acting as the hydraulic fluid. With advancing age, the collagen fibers of the annulus fibrosis becomes thinned and weakened. The nucleus pulposus may rupture through the annulus posteriorly and compress the nerve roots, a condition commonly known as a 'slipped disc'. The discs implicated in cervical injuries are between the fifth and sixth (C5-C6) vertebrae and the sixth and seventh (C6-C7) vertebrae; and in lower back injuries, the fourth and fifth lumbar (L4-5) vertebrae or the fifth lumbar and first sacral (L5-S1) vertebrae are affected most often. In cases where the disc does not rupture, nerve compression may be caused by osteophyte formation from degenerative disc disease. The osteophyte protrudes into the intervertebral foramen and compresses the nerve root resulting in continuous or intermittent chronic pain.

When a surgeon removes all or part of a ruptured disc from the back, he enlarges the hole in the annulus fibrosis through which to remove the ruptured disc and loose disc tissue in the interspace. The formed hole never heals which allows the susceptibility of additional disc rupture though the persistent hole as well as an inflammatory cascade that results from exposure of the interior of the disc to the epidural space. Inflammation and fibrosis occurs in the intervertebral space, frequently resulting in changes in the surrounding tissues including the vertebrae, hyaline plates, dura mater and the spinal cord.

About 200,000 discectomies are performed every year. Biological repair of the annular hole or defect is essential to advance the standard of care of the patient with intervertebral disc injury. The present invention addresses this repair of the annular fibrosis by use of a cultured connective tissue construct that, when surgically applied to the defect in the annulus, closes the hole to form a barrier to prevent inflammation and additional disc rupture.

SUMMARY

The invention is a method for repairing an injured intervertebral disc of a patient using a cultured connective tissue construct. The method includes modifying the opening in the annulus fibrosis of the intervertebral disc created by the disc herniation and selectively removing nucleus pulposis then grafting a cultured connective tissue construct into the opening. The closure of the annulus fibrosis is important to prevent re-hemiation of the disc and to mitigate the inflammatory response and epidural fibrosis in the cavity that may result in nerve damage. The cultured connective tissue construct is a living cultured tissue containing connective tissue cells and extracellular matrix, such as collagen. Because of the tissue-like properties of the cultured tissue construct, it is bioremodelable, meaning that it is able to undergo cell repopulation by the ingrowth of host cells, vascularization, and reorganization and replacement of matrix components of the implanted construct by host cells and enzymes.

DESCRIPTION OF THE FIGURES

The FIGURE depicts an apparatus for forming a connective tissue equivalent.

DETAILED DESCRIPTION

The invention is directed to a method of tissue replacement and repair using a cultured connective tissue construct. The connective tissue construct comprises collagen and living cells and is therefore bioremodelable, meaning that when it is grafted to a patient in need of tissue replacement and repair, it immediately functions as a replacement tissue while at the same time begins to integrate with the patient's tissue at the implant site to form a new tissue. In the most preferred embodiment, the invention is directed to a method for repairing annulus fibrosis of the intervertebral disc, after discectomy surgery where the annulus fibrosis has been opened, with a cultured connective tissue construct.

The cultured connective tissue construct is used to close the annular wall after removal of damaged intervertebral disc tissue, such as the nucleus pulposus and annulus fibrosis, after multi level discectomy for correction of spinal deformities, spinal reconstructive surgery or complete or partial removal of an injured disc due to injury such as annular tear, lesion, rupture, prolapse, hernia, or perforation. Closing the annulus by this method seals the cavity to lessen the inflammatory response and to mitigate postoperative epidural fibrosis that naturally follows after removal of the tissue from the cavity. This closure of the annulus fibrosis also prevents subsequent disc prolapse by the remainder of intervertebral disc tissue remaining in the intervertebral space and slows further disc degeneration.

The method also includes the closing of the annulus fibrosis using a cultured connective tissue construct after implantation of a disc replacement. Support of the vertebrae with a disc replacement or spacer after disc removal is sometimes performed to maintain the intervertebral disc to maintain function and to prevent nerve damage. The replacement is provided to the intervertebral space through an opening made in the annulus fibrosis, either the same one used to access the damaged disc or an additional opening. Disc replacements are used to maintain the normal disc space height to prevent impingement of the posterior facet joints. Pressure on the spinal nerves may cause pain or paralysis in the area of their distribution. Functional spacer implants transmit and attenuate compressive and torsional forces and stabilize the joint. Disc replacement materials may include metals, metallic alloys, synthetic solids and meshes, and hydrogels so long as they are biocompatible with the patient's tissues.

To remove the damaged disc, any technique known in the art of intervertebral disc removal may be employed, including, but not limited to discectomy, discotomy, laminectomy or laminotomy procedures. Depending on the type and degree of disc injury, the intervertebral disc may be accessed any number of ways including anteriorly, posteriorly, posteriolaterally. The method for accessing the intervertebral disc includes laparotomy discectomy techniques. Access through the annulus fibrosis includes uniportal and multiportal approaches where either one or more opening are made in the annulus fibrosis to remove disc material and to implant and position an intervertebral spacer prosthesis.

After discectomy is performed on the patient, the cultured connective tissue construct is inserted into the hole created in the annulus fibrosis created by the surgical procedure to seal the interior region of the intervertebral disc. Depending on the size of the patient and the size of the hole in the annulus, one or more pieces may be used to plug the hole with the pieces held in place by pressure imposed by the surrounding tissues. Optionally and additionally, a cultured connective tissue construct is applied over the opening and secured into place along the tissue boundary of the opening and the construct. When the construct is applied over the opening in the annulus, the construct may be secured in place by suture or surgical adhesive such as fibrin glue or other biologically compatible adhesives used in surgical procedures Once the procedure for grafting the construct is completed, the construct immediately assumes the function as a barrier between the cavity interior of the nucleus pulposus and the exterior of the annulus fibrosis.

In another preferred method of the invention, the cultured connective tissue construct is used in surgical repair of the central nervous system. The cultured connective tissue construct is used to seal the dura mater that covers the brain and spinal cord. The sheet construct is an appropriate form to close dural defects after injury or spinal or cranial surgery to maintain separation of the interior of the central nervous system from other bodily cells and tissues.

The cultured connective tissue construct is bioremodelable, meaning that it is able to undergo cell repopulation by the ingrowth of host cells, vascularization, and reorganization and replacement of matrix components of the implanted construct by host cells and enzymes. The graft prosthesis retains its functional characteristics while the patient's cells remodels all, or substantially all of the construct to integrate it with host tissue, and as such, is functional as an analog of the tissue it repairs or replaces.

The cultured connective tissue construct comprises connective tissue cells bound by an extracellular matrix, primarily of collagen. The extracellular matrix aspect of the construct may vary in organization and composition and still qualify as a connective tissue construct for use in the method of the invention. The connective tissue construct may be a contracted collagen lattice containing fibroblasts as described by Bell in U.S. Pat. No. 4,485,096 or by Kemp, et al. in U.S. Pat. No. 5,536,656 where the contracted collagen lattice is disposed on an acellular collagen gel, the disclosures of which is incorporated herein be reference. Another construct for use in the method is a bioengineered tissue construct of cultured cells and endogenously produced extracellular matrix components without the requirement of exogenous matrix components or network support or scaffold members such as those described in PCT Publication No. WO 00/29553 to Murphy, et al., the disclosure of which is incorporated herein by reference. Connective tissue constructs such as those that incorporate a synthetic or bioresorable mesh member having cultured fibroblasts attached and, enveloping it with endogenously produced matrix such as those described by U.S. Pat. Nos. 5,580,781, 5,443,950, 5,266,480, 5,032,508, 4,963,489 to Naughton, et al. may also be used, a fibrous collagen matrix containing cultured cells therein as described by U.S. Pat. Nos. 4,505,266 and 4,280,954 to Yannas, et al. Xenogeneic materials such as de-epidermalized and decellularized dermis, and other flat sheet tissues that have been cleaned of antigenic determinants and cellular debris can be used as a matrix component that is cultured with nonallogeneic cells to repopulate the construct.

Preferred cell types for use in this invention are derived from mesenchyme. More preferred cell types are fibroblasts, stromal cells, and other supporting connective tissue cells, or, as in the most preferred embodiment, human fibroblasts. Human fibroblast cell strains can be derived from a number of sources, including, but not limited to neonate male foreskin, dermis, tendon, lung, umbilical cords, cartilage, urethra, corneal stroma, oral mucosa, and intestine. A preferred fibroblast type is derived from dermis. The human cells may include but need not be limited to: fibroblasts, smooth muscle cells, chondrocytes and other connective tissue cells of mesenchymal origin. Embryonic progenitor cells such as mesenchymal stem cells may be used in the invention to prepare the cultured construct and induced either in vitro or in vivo to differentiate to develop into the desired tissue. It will be appreciated by the skilled artisan that the cultured connective tissue construct may contain, by either intentional addition or by result of culture of fibroblasts from primary sources, other cells found in connective tissue and other extracellular matrix components. It is preferred, but not required, that the origin of the matrix-producing cell used in the production of a tissue construct be derived from a tissue type that it is to resemble or mimic after employing the culturing methods of the invention. For instance, a construct is cultured with fibroblasts to form a living connective tissue construct; or myoblasts, for a skeletal muscle construct. More than one cell type can be used to fabricate a tissue construct.

Although human cells are preferred for use in the invention, the cells to be used in the method of the invention are not limited to cells from human sources. Cells from other mammalian species including, but not limited to, equine, canine, porcine, bovine, feline, caprine, and ovine sources may be used. Murine cells, cells from rodent sources, may also be used. Cell donors may vary in development and age. Cells may be derived from donor tissues of embryos, neonates, or older individuals including adults.

In addition, genetically engineered cells that are spontaneously, chemically or virally transfected may also be used in this invention. For those embodiments that incorporate more than one cell type, mixtures of normal and genetically modified or transfected cells may be used and mixtures of cells of two or more species or tissue sources may be used, or both. Recombinant or genetically-engineered cells may be used in the production of the tissue construct to create a tissue construct that acts as a drug delivery graft for a patient needing increased levels of natural cell products or treatment with a therapeutic. The cells may produce recombinant cell products, growth factors, hormones, peptides or proteins for a continuous amount of time or as needed when biologically, chemically, or thermally signaled due to the conditions present in culture. Cells may also be genetically engineered to express proteins or different types of extracellular matrix components which are either 'normal' but expressed at high levels or modified in some way to make a graft device comprising extracellular matrix and living cells that is therapeutically advantageous for improved wound healing, facilitated or directed neovascularization. These procedures are generally known in the art, and are described in Sambrook et al, *Molecular Cloning, A Laboratory Manual*, Cold Spring Harbor Press, Cold Spring Harbor, N.Y. (1989), incorporated herein by reference. All of the above-mentioned types of cells may be used in this invention for the production of a cultured skin construct that will synthesize the conditioned media containing cytokines.

While collagen is the most preferred extracellular matrix composition for use in the production of skin equivalents that produce and secrete cytokines to condition the culture media, other extracellular matrix components may be used. These extracellular matrix components may be used alone or, preferably, be included with the collagen to mimic native dermal matrix. These extracellular matrix components may include: other collagens, both fibrillar and non-fibrillar collagen from the collagen family such as collagen types II,III, IV, V, VI, VII, VIII, IX, X, XI, XII, XIII, XIV, XV, XVI, XVII, XVIII, XIX, other matrix proteins that may include, but are not limited to elastin, proteoglycans such as decorin or biglycan, or glycoproteins such as tenascin, vitronectin, fibronectin, laminin, thrombospondin I, and glycosaminoglycans (GAG) such as hyaluronic acid (HA). The dermal matrix may vary in composition and structure: collagen sponges, biocompatible, bioremodelable, decellularized dermis, or collagen gels. Rather than provide extracellular matrix components to the dermal cells, they can be cultured on biodegradable mesh members (such as nylon or polygalactin (PGA)) to provide a culture support and cultured to produce extracellular matrix until the cells and their matrix envelop the support. In the preferred embodiment, the cultured connective tissue construct is a contracted collagen gel, contracted by fibroblasts such as those described in U.S. Pat. No. 4,485,096 to Bell, incorporated herein by reference. In another preferred embodiment, the contracted collagen gel is disposed on a bulk acellular collagen layer on a porous membrane to anchor the gel to the membrane and to prevent excessive radial contraction of the gel. Methods for incorporating a bulk acellular collagen layer are described in U.S. Pat. No. 5,536,656 to Kemp, et al., and are incorporated herein by reference.

Both the tissue equivalent and the acellular, hydrated collagen gel in accordance with the present invention may be prepared using collagen derived from skin and tendon, including rat tail tendon, calf skin collagen, and calf extensor tendon. Other sources of collagen would be suitable. A particularly preferred collagen composition derived from calf common digital extensor tendon and methods of deriving such collagen compositions are disclosed in U.S. Pat. No. 5,106,949 to Kemp, the disclosure of which is incorporated herein by reference.

A dermal equivalent is cast directly on the bottom surface of a tissue culture dish; directly on a porous member, such as a liquid permeable membrane; or an acellular, hydrated collagen gel using procedures in accordance with the aforementioned teachings of Kemp, et al. and as described hereinafter. A casting mixture containing collagen and fibroblasts is added to inner container 20 over an acellular, hydrated collagen gel 25 and maintained under conditions that enable the tissue equivalent to form. As the tissue equivalent forms on an acellular, hydrated collagen gel 25, it contracts radially. Typically, the sides of the dermal layer 26 slope towards the outer periphery of hydrated collagen gel 25 to form a mesa as shown in the FIGURE at 52. The concentration of collagen, the number of cells and the volume of the casting mixture can be controlled to optimize the diameter and thickness of the living tissue equivalent. The casting mixture comprises cells at a concentration of about $1.25 \times 10^4$ to about $5 \times 10^4$ cells/ml and collagen at about 0.5 to about 2.0 mg/ml in a nutrient medium. A preferred cell concentration is about $2.5 \times 10^4$ cells/ml. The cultures are maintained in an incubator to ensure sufficient environmental conditions of controlled temperature, humidity, and gas mixture for the culture of cells. Preferred conditions are between about 34° C. to about 38° C., more preferably 37±1° C. with an atmosphere between about 5-10±1% $CO_2$ and a relative humidity (Rh) between about 80-90%. Once the collagen lattices have contracted, they may be used for surgical applications to treat a patient in need of tissue repair or replacement.

In one alternative embodiment of the present invention, an acellular collagen gel is formed on the culture substrate prior to the formation of the connective tissue construct to provide an anchoring means to the substrate. In some cases, the substrate requires this anchoring means and in other cases, it is not needed. When the acellular collagen gel component is utilized in the fabrication of the cultured connective tissue construct, it has been found that the ratio of the volume of the casting mixture for the tissue equivalent to the volume of the casting mixture for the acellular, hydrated collagen gel has an effect upon cell viability and differentiation. Useful ratios, volume to volume (v/v), of tissue equivalent casting mixture to collagen gel casting mixture are about 3:1 to 1:3. A preferred ratio wherein the cell concentration in the collagen lattice is at about $2.5 \times 10^4$ cells/ml is 3:1. The acellular, hydrated collagen gel 25 is prepared from a collagen composition comprising collagen at about 0.5 to 2.0 mg/ml, preferably about 0.9 to 1.1 mg/ml and nutrient media. This collagen composition is added to the inner container 20 and maintained under conditions which permit the collagen composition to set and form an acellular, hydrated collagen gel of suitable dimensions, typically about 1 to 5 mm thick, a preferred thickness range being about 2 mm to about 3 mm. An acellular, hydrated collagen gel 25 is preferably thick enough so that a portion remains acellular as cells migrate from the tissue equivalent into an acellular, hydrated collagen gel and thin enough so that the tissue equivalent is not undesirably removed from the nutrient source provided in outer container 10.

In another alternative embodiment, the cultured connective tissue construct is formed from cells grown under conditions to produce a layer of extracellular matrix which is synthesized and assembled by the cultured fibroblast cells, with the cultured fibroblast cells contained within the synthesized extracellular matrix layer, wherein the extracellular matrix is produced by the cultured fibroblast cells in the absence of exogenous matrix components or synthetic members during the culturing conditions. Procedures for fabricating these cultured connective tissue constructs are described in PCT Publication No. WO 00/29553 to Murphy, et al. the teachings of which are incorporated herein by references and described briefly below.

Once sufficient cell numbers have been obtained after isolation and scale-up, cells are harvested and seeded onto a suitable culture surface and cultured under appropriate growth conditions to form a confluent sheet of cells. In the preferred embodiment, the cells are seeded on a porous membrane that is submerged to allow medium contact from below the culture through the pores and directly above. Preferably, cells are suspended in either base or growth media and are seeded on the cell culture surface at a density between about $1 \times 10^5$ cells/cm$^2$ to about $6.6 \times 10^5$ cells/cm$^2$, more preferably between about $3 \times 10^5$ cells/cm$^2$ to about $6.6 \times 10^5$ cells/cm$^2$ and most preferably at about $6.6 \times 10^5$ cells/cm$^2$ (cells per square centimeter area of the surface). Cultures are cultured in growth medium to establish the culture and are cultured to between about 80% to 100% confluence at which time they are induced chemically by changing the medium to matrix production medium in order to upregulate the synthesis and secretion of extracellular matrix. In an alternate method, cells are seeded directly in production media to eliminate the need to change from the basic media to the production media but it is a method that requires higher seeding densities.

During the culture, fibroblasts organize the secreted matrix molecules to form a three dimensional tissue-like structure but do not exhibit significant contractile forces to cause the forming cell-matrix construct to contract and peel itself from the culture substrate. Media exchanges are made every two to three days with fresh matrix production medium and with time, the secreted matrix increases in thickness and organization. The time necessary for creating a cell-matrix construct is dependent on the ability of the initial seeding density, the cell type, the age of the cell line, and the ability of the cell line to synthesize and secrete matrix. When fully formed, the constructs of the invention have bulk thickness due to the fibrous matrix produced and organized by the cells; they are not ordinary confluent or overly confluent cell cultures where the cells may be loosely adherent to each other. The fibrous quality gives the constructs cohesive tissue-like properties unlike ordinary cultures because they resist physical damage, such as tearing or cracking, with routine handling in a clinical setting. In the fabrication of a cultured dermal construct, the cells will form an organized matrix around themselves on the cell culture surface preferably at least about 30 microns in thickness or more, more preferably between about 60 to about 120 microns thick across the surface of the membrane; however, thicknesses have been obtained in excess of 120 microns and are suitable for use in testing or clinical applications where such greater thicknesses are needed.

In still another alternative embodiment, the cultured connective tissue constructs may also be treated before application to a patient to enhance graft take or healing, or both, to the application site on the patient. The constructs may be treated with other components by contacting them with a solution containing the components, such as by immersion. Components for treating a construct before application comprises extracellular matrix components such as hyaluronic acid, collagen, proteoglycan, or glycosaminoglycans; or cytokines, including growth factors such as: basic fibroblast growth factor (bFGF), epidermal growth factor (EGF), keratinocyte growth factor (KGF), transforming growth factor alpha (TGFα), transforming growth factor beta (TGFβ), including transforming growth factor beta-1 (TGFβ1) and transforming growth factor beta-2 (TGFβ2), granulatory colony stimulating factor (GCSF), insulin-like growth factor (IGF), vascular endothelial growth factor (VEGF), and tumor necrosis factor (TNF). It should be noted that the aforementioned terms in parentheticals are abbreviations commonly known and used in the art for the formal nomenclature preceding them.

The following examples are provided to better explain the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

Preparation of a Connective Tissue Construct Comprising a Contracted Collagen Lattice Human neonatal foreskin fibroblasts (originated at Organogenesis, Inc. Canton, Mass.) were seeded at $5 \times 10^5$ cells/162 cm$^2$ tissue culture treated flask and grown in growth medium. The growth medium consisted of: Dulbecco's Modified Eagle's medium (DMEM) (high glucose formulation, without L-glutamine, BioWhittaker, Walkersville, Md.) supplemented with 10% newborn calf serum (NBCS) (HyClone Laboratories, Inc., Logan, Utah) and 4 mM L-glutamine (BioWhittaker, Walkersville, Md.). The cells were maintained in an incubator at 37±1° C. with an atmosphere of 10±1% $CO_2$. The medium was replaced with freshly prepared medium every two to three days. After 8 days in culture, the cells had grown to confluence, that is, the cells had formed a packed monolayer along the bottom of the tissue culture flask, and the medium was aspirated from the culture flask. To rinse the monolayer, sterile-filtered phosphate buffered saline was added to the bottom of each culture flask and then aspirated from the flasks. Cells were released from the flask by adding 5 mL trypsin-versene glutamine (BioWhittaker, Walkersville, Md.) to each flask and gently rocking to ensure complete coverage of the monolayer. Cultures were returned to the incubator. As soon as the cells were released 5 ml of SBTI (Soybean Trypsin Inhibitor) was added to each flask and mixed with the suspension to stop the action of the trypsin-versene. The cell suspension was removed from the flasks and evenly divided between sterile, conical centrifuge tubes. Cells were collected by centrifugation at approximately 800-1000× g for 5 minutes.

An apparatus similar to that shown in the FIGURE was used in conducting the work described herinafter. The cover is removed for conducting operation but is otherwise kept in place to maintain sterility. Pertinent information regarding the apparatus is listed: Outer container 10 has a diameter of 100 mm or more. The inner container 20 has a diameter of 75 mm. The permeable member 24 consists of a polycarbonate membrane with a pore size of about 3 μm (micron) and a thickness of 5 μm (micron).

A "premix" solution of 16.2 ml 10× Minimum Essential Medium (MEM), 1.6 ml 200 mM L-glutamine, 0.2 ml 50 mg/ml gentamycin, 18.0 ml fetal bovine serum, 5.0 ml 71.2 mg/ml sodium bicarbonate. The stock solutions were aseptically combined in the above sequence, and stored at 4° C. for approximately 30 minutes in a sterile 50 ml tube. About 27.44 ml of 2.2 mg/ml collagen solution (extracted by acid from calf common digital extensor tendon) in 0.05% v/v acetic acid, was weighed out into a 50 ml tube and stored 4° C. for 30 minutes. Dulbecco's Minimum Essential Medium (DMEM) complete (containing 10% FBS, 4 mM L-glutamine, 50 μg/ml gentamycin) was added and 1 ml aliquots were pipetted onto the membrane of the inner container 20 and allowed to gel at room temperature.

The connective tissue layer, a hydrated collagen gel containing cells, was cast with human dermal fibroblasts. A general description of procedures and reagents may also be found in U.S. Pat. No. 4,485,096 to Bell, U.S. Pat. No. 5,536,656 to Kemp, et al., and U.S. Pat. No. 5,712,163 to Parenteau, the disclosures of which are incorporated herein by reference.

The casting mixture for preparing each connective tissue construct included about 12.5 ml of the premix described above to which was added to 27.44 ml of a 2.2 mg/ml collagen solution in 0.05% v/v acetic acid, also described above, and $6.25 \times 10^5$ human dermal fibroblasts. After the components were mixed at a total volume of about 40 ml, it was dispensed into the container 20 and allowed to gel. The gelled collagen containing the suspended fibroblasts was immersed in Dulbecco's Minimum Essential Medium (DMEM) complete added to the outside container 20 and then incubated at 36° C./10% $CO_2$ for 4 to 8 days to allow the cells to contract the collagen to form a contracted collagen lattice that is a cultured connective tissue construct 52.

Example 2

Preparation of a Connective Tissue Construct of Cultured Cells and Endogenously Produced Extracellular Matrix Components Without the Requirement of Exogenous Matrix Components or Network Support or Scaffold Members Connective tissue construct of cultured cells and endogenously produced extracellular matrix components were prepared according to the teachings of Murphy, et al. disclosed in PCT Publication WO 00/29553. Human neonatal foreskin fibroblasts were cultured to expand their numbers using the procedure described in Example 1 but in a chemically defined medium, that is, containing no serum or animal-derived organ extracts. Cells were then resuspended to a concentration of $3 \times 10^6$ cells/ml, and seeded on to 0.4 micron pore size, 24 mm diameter tissue culture treated membrane inserts in a six-well tray at a density of $3.0 \times 10^6$ cells/TW ($6.6 \times 10^5$ cells/cm$^2$). Cells in this example were cultured in chemically defined medium throughout.

The medium contained: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), $1 \times 10^{-4}$ M ethanolamine (Fluka, Ronkonkoma, N.Y. cat. #02400 ACS grade), $1 \times 10^{-4}$ M o-ophosphoryl-ethanolamine (Sigma, St. Louis, Mo.), 5 µg/ml transferrin (Sigma, St. Louis, Mo.), 20 pM triiodothyronine (Sigma, St. Louis, Mo.), 5 µg/ml insulin (Sigma, St. Louis, Mo.), 0.4 µg/ml hydrocortisone (Sigma, St. Louis, Mo.), 6.78 ng/ml selenium (Sigma Aldrich Fine Chemicals Company, Milwaukee, Wis.), 50 ng/ml L-ascorbic acid (WAKO Chemicals USA, Inc.), 0.2 µg/ml L-proline (Sigma, St. Louis, Mo.), 0.1 µg/ml glycine (Sigma, St. Louis, Mo.).

Samples for histological analysis were taken at days 7, 14 and 21 and fixed in formalin, then embedded in paraffin for hemotoxylin and eosin staining for light microscope analysis. Biochemical analysis measuring the collagen content of the construct showed 170.88±9.07 µg/cm$^2$. Besides endogenously produced fibrillar collagen, decorin and glycosaminoglycan were also present in the cell-matrix constructs. The cultured dermal constructs formed comprise dermal fibroblasts and endogenously produced matrix. All have fully formed collagen fibrils in packed organization arranged between the cells. Their fibrous qualities, thickness, and cohesive integrity give the construct considerable strength to allow it to be peelably removed from the culture membrane and handled as it is transferred to a patient to be treated with the construct, as in a graft or implant.

Example 3

Use of a Connective Tissue Construct to Repair the Annulus Fibrosis After Partial Discectomy To observe the persistence of graft fibroblasts in the cultured connective tissue construct, constructs containing porcine fibroblasts labeled with Green Fluorescent Protein (GFP) are implanted in a pig model.

Six young pigs of either sex up to 50 kg are housed individually for a minimum of two days prior surgery while fed with standard pig chow.

Experimental animals are pre-anesthetized with Telazol and atropine and ihtubated. They are placed on inhalation gas of isoflurane and oxygen and kept in surgical plane of anesthesia. They are also administered an antibiotic.

Defects in the discs are created by making a 5×10 mm incision in the annulus followed by a standard discotomy with equal nuclear removal at each space. A total of three discs are operated on per pig. Two sites are treated with cultured connective tissue constructs with GFP labeled fibroblasts and the remaining site serves as a control. To apply the connective tissue construct, it is first trimmed into three or four smaller pieces and then inserted into the annular hole opening. Two animals are euthanized on each of weeks 2, 4, and 6 and the surgical sites are removed. The discs are placed in formalin and then 70% ethanol prior to histological processing. The discs are serially sectioned and examined under fluorescence for evidence of GFP labeled fibroblasts.

Example 4

Use of a Connective Tissue Construct With a Intervertebral Disc Spacer to Maintain the Intervertebral Space.

To observe the persistence of graft fibroblasts in the cultured connective tissue construct, constructs containing fibroblasts are implanted in a pig model.

Six young pigs of either sex up to 50 kg are housed individually for a minimum of two days prior to surgery while fed with standard pig chow.

Experimental animals are pre-anesthetized with Telazol and atropine and intubated. The are placed on inhalation gas of isoflurane and oxygen and kept in surgical plane of anesthesia. They are also administered an antibiotic.

Defects in the discs are created by making a 5×10 mm incision in the annulus fibrosis followed by a standard discotomy with equal nuclear removal at each space. A total of three discs are operated on per pig.

Through the hole made in the annulus fibrosis, the intervertebral space is opened and the disc is removed, restricted to the anterior and middle third portion. The intervertebral disc spacer comprising Dacron mesh and hydrogel is placed into the thoracic cavity by passing it through the hole in the annulus fibrosis. The good position of the implant is ascertained using radiologic procedures and then the spacer is then fixed into place. The cultured connective tissue construct is then applied to the annular opening by first trimming the construct to the size of the annular hole opening and then sutured to the tissue surrounding the opening of the space using resorbable sutures. While all three sites are provided with an intervertebral disc spacer, two sites are treated with cultured connective tissue constructs and the remaining site serves as a control.

Two animals are euthanized on each of weeks 2, 4, and 6 and the surgical sites are removed. The discs are placed in formalin and then 70% ethanol prior to histological processing. The discs are serially sectioned and examined under fluorescence for evidence of GFP labeled fibroblasts.

In all specimens, the intervertebral disc spacer maintained its original placement. In control specimens, the nucleus pulposus showed a significant loss of proteoglycans and collagen and an increase in other non-collagenous proteins in the cavity. In experimental specimens, the connective tissue construct forms a complete scar over the opening made in the annular fibrosis. The biochemical make up of the cavity had changed somewhat but was closer to composition of the negative control specimens, indicating that fibrosis of the cavity had been substantially prevented by the closure of the annulus after disc injury.

Example 5

A Time Course Study Using Connective Tissue Constructs in Annulus Fibrosis Repair of Pigs Discectomy to remove ruptured and expulsed nucleus pulposus is a common clinical practice to relieve pain and neurologic disturbance. The procedure creates a defect in annulus fibrosis that is often filled by fibrotic tissues, a situation that eventually leads to collapse of the intervertebral disc and requires fusion of the adjacent vertebral segments.

Porcine connective tissue constructs were prepared using porcine dermal fibroblasts transfected to express green fluorescent protein (GFP) according to the methods of Examples 1. Each construct was made up of type I bovine collagen containing 20 to 30 million viable GFP-transfected porcine dermal fibroblasts and were about 2 mm in thickness. The purpose of this study was to evaluate the feasibility of connective tissue constructs for repair of the annulus fibrosis in a porcine model and to determine the biocompatibility, persistence and remodeling of the constructs in this model.

Six 3 to 4 month-old pigs were used for the study. Three consecutive vertebral discs were posteriorly exposed through a laminotomy approach for each animal. A surgical annular defect was created in each exposed disc. Several pieces of connective tissue construct, each about 2 to 5 mm in diameter, were implanted into two defects of each animal. The other disc defect was left empty as a control. The pigs were euthanized, in groups of two, at two, four and six weeks post implant. The vertebral columns containing operated discs were removed and fixed in 10% neutral buffered formalin. Bright field microscopy was done on hemotoxilin and eosin stained sections for general evaluation, and fluorescent microscopy was done on unstained sections for identifying green fluorescent protein labeled cells.

Microscopy revealed clear evidence of implanted connective tissue construct remnants, including viable fluorescent fibroblasts, in several of the treated annuli from the two animal groups euthanized at two and four weeks. There was also identifiable remodeling of the connective tissue construct remnants by the host tissue. The implanted defects showed less inflammation and more advanced healing than controls at all time points. The implanted defects had cartilaginous tissue bridging the opening, whereas the control defects still had a significant amount of fibrotic tissue. The results from this feasibility study indicate that the implanted pig connective tissue construct was biocompatible to the host tissue, can persist up to 4 weeks, and enhance reparative activities of the annulus by 6 weeks.

Although the foregoing invention has been described in some detail by way of illustration and example for purposes of clarity and understanding, it will be obvious to one of skill in the art that certain changes and modifications may be practiced within the scope of the appended claims.

We claim:

1. A method for repairing an intervertebral disc of a patient using a cultured connective tissue construct, comprising:
    (a) forming at least one opening in the annulus fibrosis of the intervertebral disc;
    (b) removing at least a portion of the nucleus pulposus through the opening in the annulus fibrosis;
    (c) inserting one or more cultured connective tissue constructs into the opening of the annulus fibrosis; and
    (d) subsequently grafting an additional cultured connective tissue construct to close the opening with the one or more cultured connective tissue constructs in the annulus fibrosis, wherein the cultured connective tissue constructs comprise:
    an extracellular matrix layer; and
    cultured fibroblast cells that synthesize and assemble the layer of extracellular matrix in the absence of exogenous matrix components or synthetic members.

2. The method of claim 1, wherein the extracellular matrix layer further comprises collagen.

3. The method of claim 1, wherein the one or more cultured connective tissue constructs are grafted into the opening in the annulus fibrosis.

4. The method of claim 1, wherein the fibroblast cells are cultured in a chemically defined medium.

5. The method of claim 1, wherein the connective tissue constructs further comprise decorin and glycosaminoglycan.

6. A method for repairing an intervertebral disc of a patient using a cultured connective tissue construct, comprising:
    (a) forming at least one opening in the annulus fibrosis of the intervertebral disc;
    (b) removing at least a portion of the nucleus pulposus through the opening in the annulus fibrosis;
    (c) inserting one or more cultured connective tissue constructs into the opening of the annulus fibrosis; and
    (d) subsequently grafting an additional cultured connective tissue construct to tissue surrounding the one or more cultured connective tissue constructs and the opening, the additional connective tissue construct closes the opening in the annulus fibrosis, wherein the cultured connective tissue constructs comprise:
    an extracellular matrix layer; and
    fibroblast cells that are cultured in a chemically defined medium in the absence of exogenous matrix components or synthetic members.

7. The method of claim 6, wherein the cultured fibroblast cells synthesize and assemble the layer of extracellular matrix in the absence of exogenous matrix components or synthetic members.

8. The method of claim 6, wherein the cultured connective tissue constructs further comprise decorin and glycosaminoglycan.

9. A method for repairing an intervertebral disc of a patient using a cultured connective tissue construct, comprising:
    (a) preparing a bioremodelable cultured connective tissue construct that comprises an extracellular matrix layer and cultured fibroblast cells by the method comprising:
        a. seeding and culturing fibroblast cells to synthesize an extracellular matrix on a cell culture surface in a medium in the absence of exogenous tissue matrix components or synthetic members;

b. inducing the cells to upregulate the synthesis and secretion of extracellular matrix; and c. culturing the cells on the cell culture surface to produce a layer of extracellular matrix of at least about 30 microns thick comprising extracellular matrix and fibroblast cells;

(b) forming at least one opening in the annulus fibrosis of the intervertebral disc;

(c) removing at least a portion of the nucleus pulposus through the opening in the annulus fibrosis;

(d) inserting at least a first cultured connective tissue construct into the opening of the annulus fibrosis; and (e) subsequently suturing a second cultured connective tissue construct to tissue surrounding the at least first cultured connective tissue constructs and the opening, the additional connective tissue construct closes the opening in the annulus fibrosis, wherein the cultured connective tissue constructs comprise:

an extracellular matrix layer; and fibroblast cells that are cultured in a chemically defined medium in the absence of exogenous matrix components or synthetic members.

10. The method of claim 9, wherein the medium is a chemically defined medium.

11. The method of claim 9, wherein the cultured connective tissue constructs comprise decorin and glycosaminoglycan.

12. The method of claim 9, wherein inducing the cells to upregulate the synthesis and secretion of extracellular matrix comprises changing the medium to matrix production medium.

13. The method of claim 9, wherein the cells are seeded directly in a matrix production medium that induces the cells to upregulate the synthesis and secretion of extracellular matrix.

* * * * *